US008348841B2

(12) United States Patent  
Varadan

(10) Patent No.: US 8,348,841 B2  
(45) Date of Patent: Jan. 8, 2013

(54) WIRELESS NANOTECHNOLOGY BASED SYSTEM FOR DIAGNOSIS OF NEUROLOGICAL AND PHYSIOLOGICAL DISORDERS

(75) Inventor: Vijay K. Varadan, Fayetteville, AR (US)

(73) Assignee: The Board of Trustees of the University of Arkansas, Fayetteville, AR (US)

( * ) Notice: Subject to any disclaimer, the term of this patent is extended or adjusted under 35 U.S.C. 154(b) by 205 days.

(21) Appl. No.: 12/757,552

(22) Filed: Apr. 9, 2010

(65) Prior Publication Data

US 2011/0251469 A1    Oct. 13, 2011

(51) Int. Cl.
*A61B 5/00* (2006.01)
(52) U.S. Cl. .......................... 600/301; 600/300
(58) Field of Classification Search .......... 600/300–301, 600/529–536, 587
See application file for complete search history.

(56) References Cited

U.S. PATENT DOCUMENTS

| | | | |
|---|---|---|---|
| 6,516,665 B1 | 2/2003 | Varadan et al. | |
| 6,984,332 B2 | 1/2006 | Varadan et al. | |
| 7,593,767 B1 * | 9/2009 | Modarres | 600/544 |
| 7,972,277 B2 * | 7/2011 | Oki et al. | 600/532 |
| 8,047,049 B2 * | 11/2011 | Daniel et al. | 73/11.04 |
| 2007/0191704 A1 * | 8/2007 | DeCharms | 600/411 |
| 2008/0071150 A1 * | 3/2008 | Miesel et al. | 600/301 |
| 2008/0277648 A1 * | 11/2008 | Wakita | 257/40 |
| 2009/0275852 A1 * | 11/2009 | Oki et al. | 600/532 |
| 2009/0318794 A1 * | 12/2009 | DeCharms | 600/410 |
| 2010/0094103 A1 * | 4/2010 | Kaplan et al. | 600/301 |
| 2010/0180701 A1 * | 7/2010 | Daniel et al. | 73/866.1 |
| 2010/0240982 A1 * | 9/2010 | Westbrook et al. | 600/391 |

OTHER PUBLICATIONS

Jung, S. et al., "Point-of-care temperature and respiration monitoring sensors for smart fabric applications," J. Smart Mater. Struct. (2006) 15:1872-1876.
Jung, S. et al., "Temperature sensor using thermal properties in the subthreshold regime of an organic thin film transistor," Applied Physics Letters (2007) 90:062105-062110.
Kapur, V. et al., "The medical costs of undiagnosed sleep apnea," Sleep (1999) 22(6):745-749.
Kumar, R. et al., "Reduced mammillary body volume in patients with obstructive sleep apnea," Neuroscience Letters (2008) 438:330-334.
Rai, P. et al., "Drain current centric modality: Instrumentation and evaluation of ISFET for monitoring myocardial ischemia like variations in pH and potassium ion concentration," IEEE Sensors Journal (2009) 9(12):1987-1995.

(Continued)

*Primary Examiner* — Henry M Johnson, III
*Assistant Examiner* — Bobby Soriano
(74) *Attorney, Agent, or Firm* — Michael Best & Friedrich LLP

(57) ABSTRACT

A wireless system for neurological and physiological monitoring of a patient. The system includes a patient monitoring unit having a headcap and a belt. The headcap includes a wireless communication module, an antenna, and an amplifier. The headcap further includes at least one of a biopotential electrode, a temperature sensor, a rotation sensor, an accelerometer, and an airflow sensor. The belt includes a respiration sensor comprising a carbon nanotube-based strain sensor. The system also includes a base receiver-server unit including a wireless receiving unit, a data storage unit, and a network communications unit. The system also includes a client monitoring unit which includes a processor, a network communications unit operably coupled to the processor, and a storage medium operably coupled to the processor, wherein the storage medium includes program instructions executable by the processor for receiving and processing data from the patient monitoring unit.

22 Claims, 17 Drawing Sheets

OTHER PUBLICATIONS

Ramachandran, V. et al., "Potassium ion sensing with nanowire electrodes on a flexible substrate for early detection of myocardial ischemia," J. Nanotech. Engin. Med. (2010) 1:011008-1-011008-5.

Young, T. et al., "Epidemiology of obstructive sleep apnea: a population health perspective," Am. J. Respir. Crit. Care Med. (2002) 1217-1239.

* cited by examiner

WIRELESS NANOTECHNOLOGY BASED SYSTEM FOR DIAGNOSIS OF NEUROLOGICAL AND PHYSIOLOGICAL DISORDERS

FIELD OF THE INVENTION

The invention relates to a system for remote monitoring and assessment of neurological and physiological disorder-related data from a patient.

BACKGROUND

Measurement of bio-potentials is important in neurological and physiological monitoring, as this allows physicians to monitor and study the functioning of patient's body including the heart and brain. The electroencephalogram (EEG) is a record of the electric signals generated as a result of the brain activity which can be detected at the skin surface. EEG is useful, (a) in monitoring sleep quality and alertness, (b) in clinical applications, for diagnosis and treatment of patients suffering from epilepsy, Parkinson's disease and other neurological disorders, and (c) continuous monitoring of fatigue, alertness of personnel deployed in the field or working under strain. We have developed and evaluated both dry and gel-wet EEG electrodes for monitoring of the brain activity. In this protocol, we focus on two major areas; (1) development of a vertically aligned carbon nanotube/nanowire and gold nanowire array for neurological and physiological monitoring, and (2) development of a wireless nanosensor network system with a low-noise, multi-channel biopotential data acquisition system.

Sleep disorders and sleep deprivation affect more than thirty million people, while another six million have moderate to severe sleep apnea in which breathing briefly stops. That is nearly one in five Americans, making sleep apnea as prevalent as asthma or diabetes. More than six million people have restless leg syndrome and periodic limb movement disorder which jolts them awake repeatedly. As many as twenty-five million people remain undiagnosed and untreated which will account for over $22 billion in unnecessary health care costs. Apart from physical factors such as obesity, studies have shown that the cumulative long-term effects of sleep loss and sleep disorders are associated with a wide range of serious health consequences and many life threatening illnesses including increased risk of hypertension, diabetes, depression, heart attack, impotence and stroke, to name a few. In addition, a significant percentage of severe traffic and industrial accidents may be caused by the involuntary human transition from wakefulness to sleep.

There are also apparent links between deficits in brain chemistry and obstructive sleep apnea (OSA) and REM sleep behavior disorder (RBD). Both are relatively common sleep problems that disturb the slumber and daytime behavior of millions of Americans. It has been reported that multiple system atrophy (MSA), a rare and fatal degenerative neurological disease, is almost always accompanied by severe sleep disorder. Patients with the fewest dopamine-producing neurons in the striatum of their brains had the worst RBD symptoms, talking and violent flailing during their sleep. People with OSA show tissue loss in brain regions that help store memory, thus linking OSA with memory loss and Alzheimer's disease. Obstructive sleep apnea, in which breathing temporarily stops during a person's sleep, often affects adults but goes undiagnosed in many cases. Its most notable symptoms are snoring and excessive daytime sleepiness, though it can also affect blood pressure, memory and even reaction-time while driving. The sleep disorders are generally undiagnosed and untreated, and hundreds of billions of dollars a year are spent due to its related problems on medical costs associated with doctor visits, hospital services, prescriptions, and over-the-counter medications.

Currently-available sleep monitoring systems use electrical recording where the electrodes make contact with the patient's skin using a conducting gel. The electrode wires are connected to a processing recording system. The subject has to be in close proximity of these machines due to the direct electrical connections with the body and the machine. The conductive gel along with many wires connected to the biopotential electrodes makes them uncomfortable for the subject, with the result that recording and monitoring of the patient's sleep patterns can become very difficult. The patient has to be in a sleep lab and/or a hospital at all times, and at least one technician needs to watch the patient's sleep behavior via video. The patient may not experience normal sleep patterns under such environments and as such the diagnostic results are not really very conclusive. Moreover, the current sleep lab test systems require a significant facility investment, large instrument capital expenditure (more than $20,000/bed), plus the use of many (twenty or more) uncomfortable patient wired sensors requiring considerable set-up labor costs. A downside of current methods is that there is no quantifying measurement adopted for the sleep studies, and the actual sleeping pattern can be monitored only when the patient is home and monitored in their own bed, not at the sleep lab bed or hospital bed, where the environments are totally different.

SUMMARY

Thus, there is a need for a low cost, reliable, and ubiquitous patient monitoring system that can be used for sleep monitoring. What is needed is a robust and non-disruptive monitoring system that addresses continuous biopotential measurements, which can analyze and record the required parameters while the patient is at home and sleeping in his or her own bed. Features, in some embodiments, include a wearable patient monitoring unit for seamless home-based sleep apnea monitoring and a wireless wearable unit for continuous monitoring, along with remote cyber access capabilities, to provide minimal intrusion in the patient's everyday life. A system for complete monitoring of sleep apnea could also include a system at the patient's home that unobtrusively measures biopotential signals along with respiration, temperature and movements. While the examples referred to herein focus on sleep monitoring, those skilled in the art will recognize that the disclosed system could be adapted for other types of remote patient monitoring.

In one embodiment, the invention includes a wireless system for physiological monitoring of a patient. The system includes a patient monitoring unit having a headcap and a belt. The headcap includes all or certain of the following sensors: a series of individual or a plurality of conventional biopotential electrodes, and/or dry biopotential electrodes including carbon nanotube array and/or gold nanowire array, a temperature sensor, a rotation sensor, an accelerometer, The headcap also includes in an embedded form factor or in a separate tethered small box form factor a wireless communication module, an antenna, and an amplifier. The belt includes a respiration sensor comprising a carbon nanotube-based strain sensor. Other integrated sensors which can be included are pulse oximetry, accelerometers and gyroscopes for limb movement, air flow sensors, dry electrode EKG sensors, and temperature sensors. The system also includes a base receiver-server unit including a wireless receiving unit, a data storage unit, and a network communications unit. The system further includes a client monitoring unit, where the client monitoring unit includes a processor, a network communications unit operably coupled to the processor, a storage medium operably coupled to the processor, wherein the storage medium includes program instructions executable by the processor for receiving and processing data from the patient monitoring unit.

In another embodiment, the invention includes a wireless system for neurological and physiological monitoring of a patient. The system includes a patient monitoring unit having a headcap and a belt. The headcap includes a wireless communication module, an antenna, and an amplifier. The headcap further includes at least one of a biopotential electrode, a temperature sensor, a rotation sensor, an accelerometer, and an airflow sensor. The belt includes a respiration sensor comprising a carbon nanotube-based strain sensor. The system also includes a base receiver-server unit including a wireless receiving unit, a data storage unit, and a network communications unit. The system also includes a client monitoring unit which includes a processor, a network communications unit operably coupled to the processor, and a storage medium operably coupled to the processor, wherein the storage medium includes program instructions executable by the processor for receiving and processing data from the patient monitoring unit.

In still another embodiment, the invention includes a patient monitoring unit for neurological and physiological monitoring of a patient. The patient monitoring unit includes a headcap including a wireless communication module, an antenna, and an amplifier. The headcap further includes at least one of a biopotential electrode, a temperature sensor, a rotation sensor, an accelerometer, and an airflow sensor.

In various embodiments, the sensors for measuring biopotentials are connected to a miniature wireless transceiver integrated into, or in a separate tethered small box form factor connected to, the headcap which is in communication with a base receiver-server unit (BRU) in the vicinity of the patient. This real-time data transfer system can use an Internet, or cellular, e.g. GSM/GPRS network and can be connected to healthcare professionals and hospitals, permitting access to a patient's conditions at most times. A patient can wear this wireless nanotechnology-based headcap monitoring system without disturbing their normal sleep patterns. The patient monitoring unit (PMU) can produce an electroencephalogram (EEG), electrocardiogram (ECG/EKG), electrooculogram (EOG), and electromyogram (EMG), as well as data pertaining to respiration, temperature, motion, and rotation and other physiological parameters of a subject and wirelessly transmit this data to a base station.

According to embodiments of the invention, the BRU includes a single-board computer, data processor, and a wireless unit to connect to a network such as the cellular network and/or the Internet. The client monitoring application (CMA) can be a data receiving and analysis program that can be installed in any personal computer, laptop computer, PDA or at the nurse's/physician's office in the hospital. The CMA receives and analyzes the data generated by the PMU and sent via the BRU.

Embodiments of the present invention include a system for wirelessly collecting electroencephalogram (EEG) electric signals generated as a result of the brain activity and measurement of bio-potentials for physiological monitoring of functioning of the body including the brain, the heart, and the respiratory system.

Embodiments of the invention include methods of monitoring the neurological and/or physiological condition of a patient. The methods include steps of providing the patient with a patient monitoring unit, the patient monitoring unit including a headcap, an optional belt or garment to be worn on the patient's torso, as well as additional sensors or probes on, in, or near the patient's body. The patient monitoring unit includes one or more electrodes and/or sensors for monitoring at least one neurological or physiological parameter of the patient, where the electrodes and/or sensors are configured for wired or wireless communication. The neurological or physiological parameters to be monitored include body effort, body position, heart rate, airflow, chest effort, abdomen effort, leg movement, pulse oximetry, electroencephalogram (EEG), electrocardiogram (ECG/EKG), electrooculogram (EOG), electromyogram (EMG), and other parameters disclosed herein. The methods can also include providing a home monitoring/base receiver-server unit which receives signals from the patient monitoring unit, in a wired or wireless manner, and transmits some or all of the signal information to a central monitoring unit. The central monitoring unit, which can be remote from the site of the patient monitoring unit and/or home monitoring/base receiver-server unit, includes a computer system and software configured for collection and analysis of data. The methods can include one or more of the following steps: remotely monitoring the patient, collecting data, transmitting the data from the patient monitoring unit to the home monitoring/base receiver-server unit, transmitting data from the home monitoring/base receiver-server unit to the central monitoring unit, analyzing the data, diagnosing the patient, and treating the patient. The methods can be used to monitor, diagnose, and/or treat various conditions such as those disclosed herein including, but not limited to, sleep apnea.

In various embodiments, the invention covers in detail a sleep apnea monitoring system based on nanotechnology-based devices in the headcap and low cost flexible nanosensors for measuring EKG and respiration, as well as accelerometers and gyroscopes for measuring leg and body movements and pulse oximetry, airflow, and temperature sensors. The system also has applications in (a) in clinical settings, for diagnosis and treatment of patients suffering from epilepsy, Parkinson's disease and other neurological disorders, (b) continuous monitoring of fatigue, alertness of personnel deployed in field or working under strain, and (c) brainwave-based control of the body or mechanical motor functions such as controlling a wheelchair.

In particular embodiments of the invention, the system includes a smart headcap for measuring EEG, EMG, and EOG, as well as optional tethered or lightweight wireless sensors for monitoring body effort, body position, heart rate, airflow, chest effort, abdomen effort, leg movement, and pulse oximetry, to name a few possibilities. The system can include three units, namely, a patient monitoring unit (PMU), which includes a headcap and a respiration sensor; a base receiver-server unit (BRU); and a client monitoring application (CMA). The base receiver-server unit (BRU) includes a compact, single-board computer (which could be as small as 5 cm×5 cm), a data processor, and a wireless unit to connect to the cellular network/internet via Wi-Fi. The client monitoring application (CMA) including a data receiving and analysis program that can be installed in any personal computer, laptop computer, or PDA. The inventive smart monitoring and therapeutic intervention system can be used for long-term, real-time sleep monitoring using conventional (i.e. gel/wet) or dry nanoelectrode-based (e.g. carbon nanotubes or gold nanowires) sensors and wireless communication modules.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
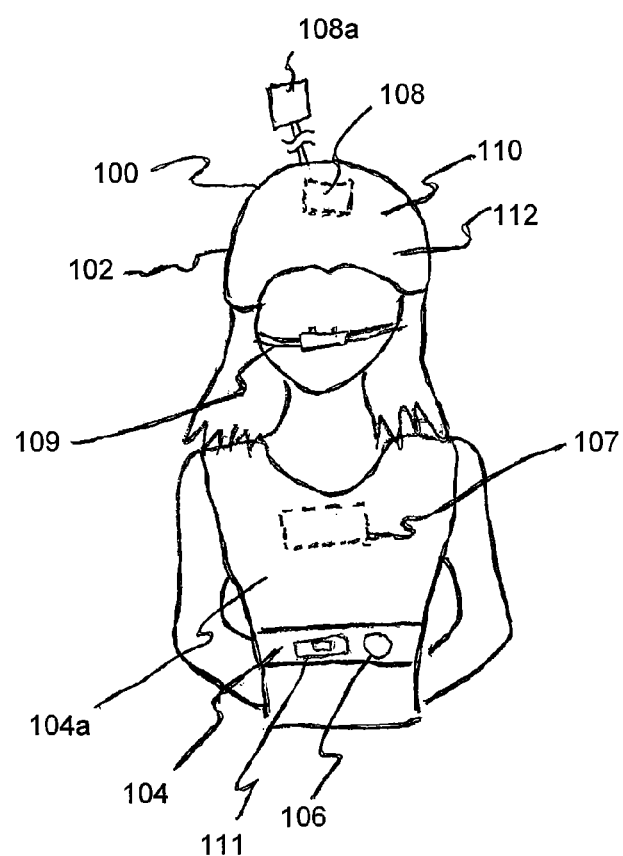
FIG. 1A shows a schematic diagram of a subject wearing a headcap and a belt including a respiration sensor.
Figure 1B:
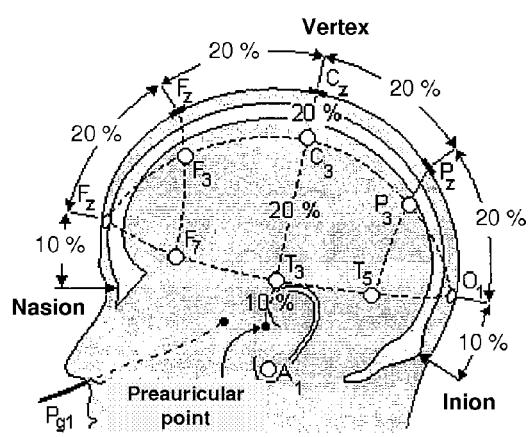
FIGS. 1B and 1C show positions of sensors on a patient's head for the headcap of FIG. 1A.
Figure 1C:
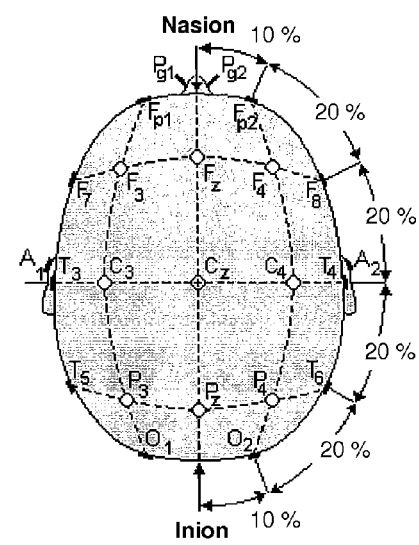
Figure 1D:
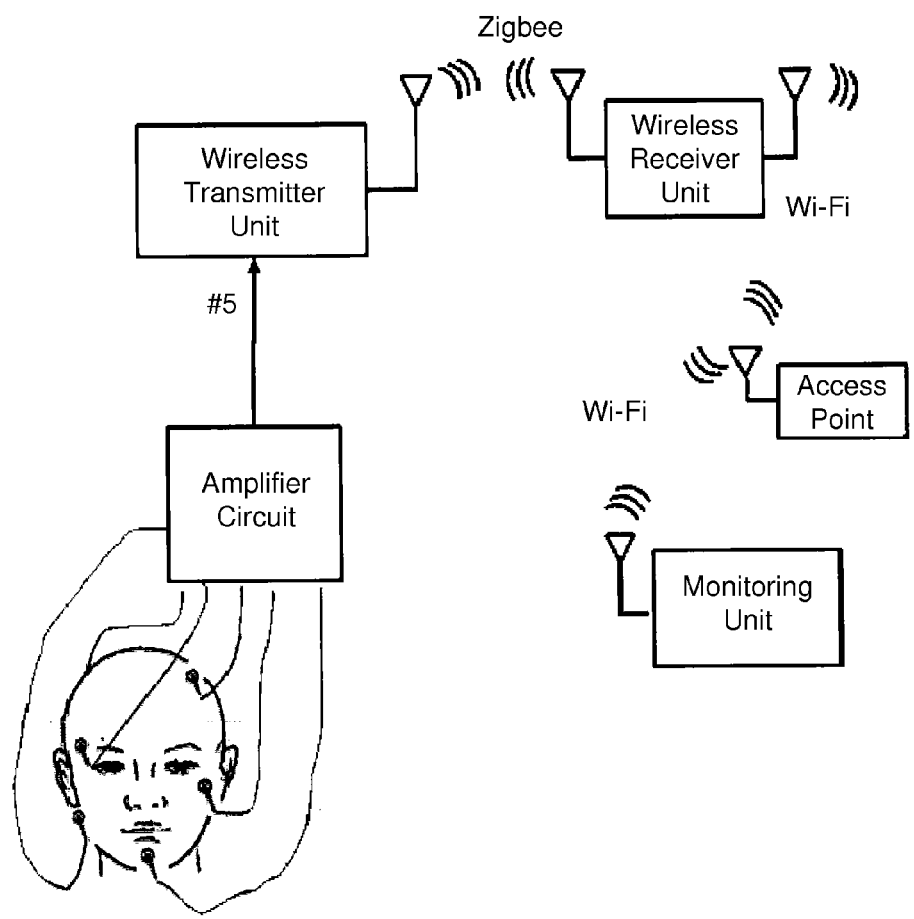
FIG. 1D shows a patient with electrodes attached for conducting EOG and/or EMG measurements.

FIG. 1A shows a schematic diagram of a subject wearing a patient monitoring unit (PMU) 10 in accordance with an embodiment of the invention. Although the system disclosed herein is presented in the context of use with a human patient, the disclosed apparatus and methods can be adapted for use on non-human animals as well. Further, the 'patients' may include healthy, normal subjects, e.g. in a research study, in addition to patients who have one or more medical conditions that are being monitored and/or diagnosed. The PMU 10 includes a headcap 100 and an optional belt 104. The headcap 100 may include one or more sensors for monitoring the patient such as standard electrodes or nanotube- or nanowire-based integrated electrodes 102, a wireless module and antenna 108, one or more rotation sensors 110, and one or more accelerometers 112, along with circuits for signal conditioning and other functions. The wireless module and antenna 108 may be contained in a form factor embedded in the headcap 100 (designated 108 in FIG. 1A) or as a separate tethered small box form factor connected to the headcap 100 (designated 108a in FIG. 1A). One or more of the various sensors and electrodes disclosed herein, whether associated with the headcap 100 or belt 104, may also be contained within form factors that are embedded in or tethered to the headcap 100 or belt 104. FIGS. 1B and 1C show the locations of various electrodes labeled $F_x$, $T_x$, $P_x$, $C_x$, and $O_x$, indicating possible arrangements of electrodes 102 on the headcap 100 according to embodiments of the invention, although other arrangements are also possible. In addition, various sensors for measuring other parameters such as temperature, pulse oximetry, etc. can also be incorporated into the headcap 100. In various embodiments, additional electrodes or sensors can also be attached, separate from the headcap 100, directly onto the patient's skin, e.g. for conducting EOG and/or EMG measurements as shown in FIG. 1D. The lines shown running from the electrodes to a single amplifier circuit in FIG. 1D are schematic only, as each sensor may in fact be a self-contained unit, or multiple sensors may be grouped together, to communicate wirelessly to the BRU 250.

Figure 1E:
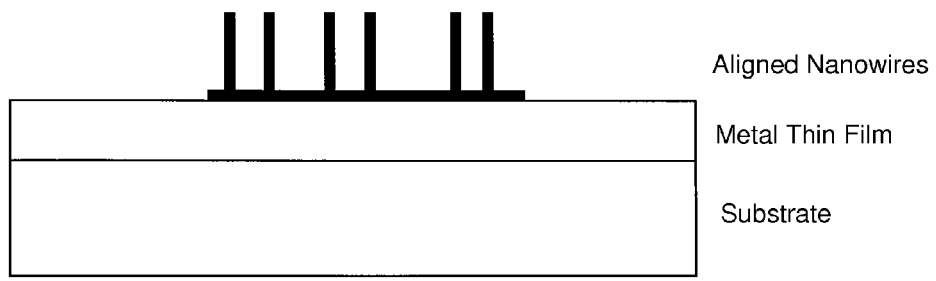
FIG. 1E shows a diagram of nanowires on a metal thin film on top of a substrate as can be employed in a biosensor.
Figure 1F:
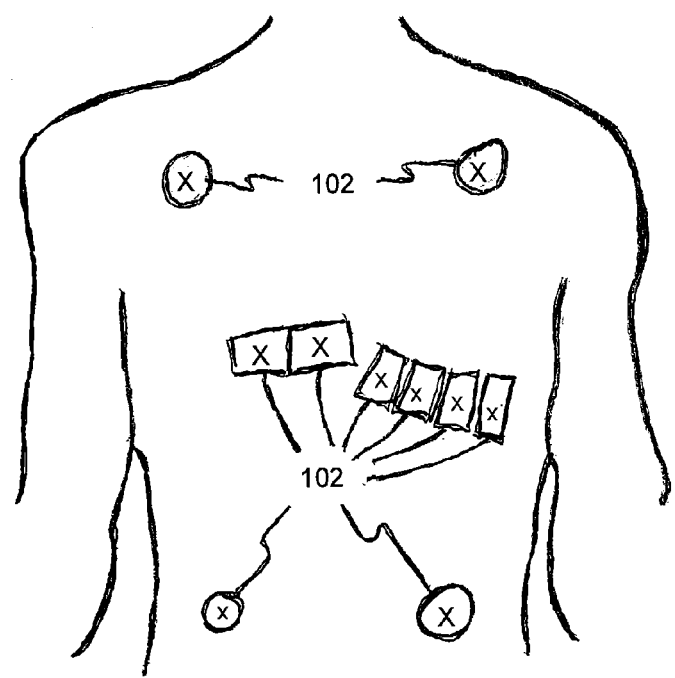
FIG. 1F shows a diagram of placement of electrode leads for a twelve-electrode EKG measurement.
Figure 1G:
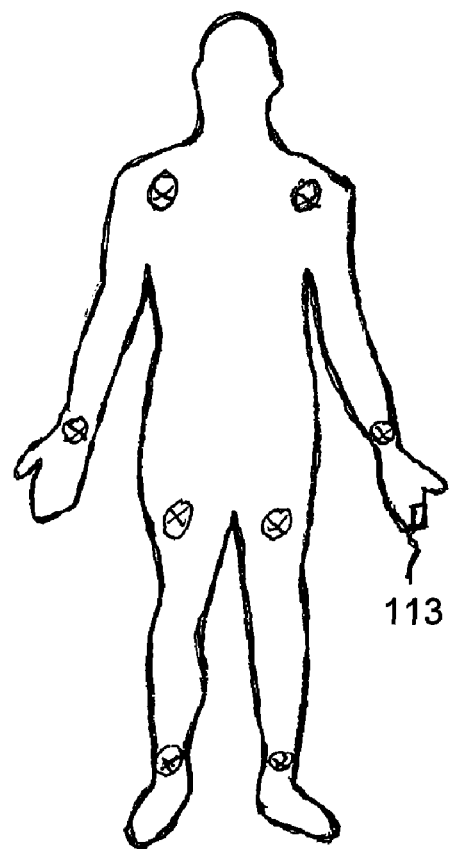
FIG. 1G shows a diagram of positioning of a pulse oximetry sensor as well as possible locations of other electrodes or sensors.

In still other embodiments, the headcap 100 and/or belt 104 may include one or more wired or wireless connections for communicating with pH and/or potassium sensors 107 that have been previously implanted in the patient (FIG. 1A). These sensors measure the patient's blood levels of pH and/or potassium, which measurements can help predict the onset of heart attack, among other health conditions (see V. Ramachandran, H. Yoon and V. K. Varadan, "Potassium ion sensing with nanowire electrodes on a flexible substrate for early detection of myocardial ischemia", Journal of Nanotechnology in Engineering and Medicine, 1. pp. 011008-1, 011008-5, 2009; P. Rai, S. Jung, T. Ji and V. K. Varadan, "Drain current centric modality: Instrumentation and evaluation of ISFET for monitoring myocardial ischemia like variations in pH and potassium ion concentration", IEEE Sensors Journal, 9, pp. 1987-1995, 2009; each of which is incorporated herein by reference). Still other sensors which can be included are air flow sensors 109 to measure air flow from the patient's mouth and/or nasal passages (FIG. 1A); piezoelectric chest and/or abdominal effort sensors 111 incorporated into the belt 104 (FIG. 1A); and a pulse oximetry sensor 113 attached to the patient's fingertip (FIG. 1G).

In various embodiments, the headcap 100 may be integrated into conventional headwear such as a hat or cap, making the headcap 100 comfortable for the patient to wear without hindering, inhibiting, or otherwise affecting the normal sleep of an individual. The belt 104 can include additional sensors, such as a respiration sensor 106 as illustrated. The belt 104 may be of varying widths and may be made of a number of suitable materials, although in general the belt 104 should be tight enough to keep the respiration sensor 106 and any other sensors or electrodes adjacent to the patient's midsection but should have sufficient elasticity to permit the patient to breathe and move comfortably. In some embodiments, the belt 104 may be enlarged to cover a substantial portion of the patient's torso and include a number of additional sensors for performing ECG/EKG and/or EMG measurements. For ECG/EKG measurements in particular, the electrodes are suitably arranged across the patient's chest, as is known to those of skill in the art, so as to obtain appropriate electrical readings to track heart activity. For example, a so-called twelve-lead EKG electrode arrangement can be performed with ten electrodes 102 located on a patient's torso (FIG. 1F); other electrode arrangements are also possible. Additional wrist, ankle, leg, and/or arm bands with electrodes or sensors may also be used for EKG/ECG and/or for other measurements, including for example one or more accelerometers to measure arm or leg motion (FIG. 1G). In each instance, one or more of the electrodes may be wired or wireless dry nanowire- or nanotube-based electrodes. In some embodiments, the belt 104 is actually a snug-fitting, shirt-like garment 104a, covering the entire torso and including openings for the patient's arms. In still further embodiments, one or more sensor or electrode may be attached to the patient's skin using adhesive, for example in order to add additional sensors or electrodes in a region that is not covered by the headcap 100 or belt 104/104a, and/or to maintain a sensor or electrode in a particular location without moving.

In certain embodiments, the rotation sensors 110 and accelerometer 112 as indicated in FIG. 1A are microelectromechanical system (MEMS) units integrated within the PMU 10. In various embodiments, a gyroscopic mechanism (in accordance with U.S. Pat. Nos. 6,984,332 and 6,516,665, each of which is incorporated herein by reference in its entirety) is used to implement the rotation sensors 110 and accelerometer 112. Rotation sensors 110, accelerometer 112, and/or gyroscopes may be attached to one or more of the patient's limbs to monitor limb movements.

Figure 2A:
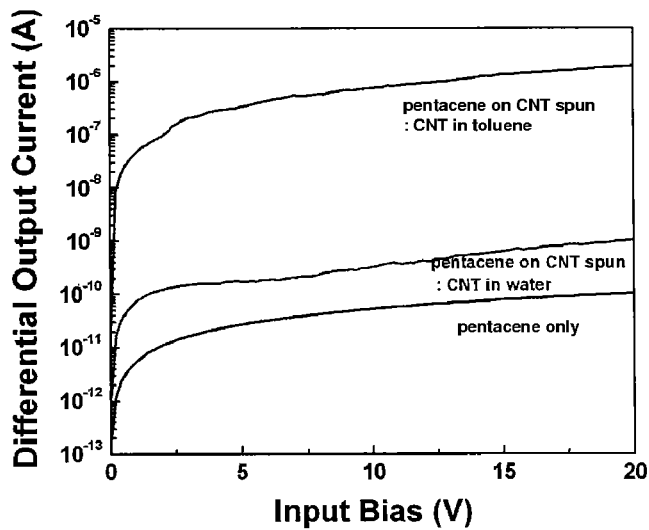
FIG. 2A shows the output of several types of organic semiconductor strain sensors.

In some embodiments, the respiration sensor 106 employs a strain sensor that is based on organic semiconductors, which in various embodiments incorporate carbon nanotubes. Inorganic semiconductors such as amorphous and microcrystalline silicon have recently been envisioned as strain sensing elements which can overcome the limitations of conventional strain sensors that are based on metallic foil and crystalline silicon. However, the high Young's modulus (~200 GPa) of the inorganic materials limits the use for applications with flexible polymeric substrates due to the large stiffness mismatch that is generated in the interface of the inorganic semiconductor elements and the flexible films. The stiffness mismatch can lead to irreversible plastic substrate deformations, degrading the sensor performance in terms of reliability and repeatability. Thus, the use of organic semiconductors with low Young's modulus (5 GPa) as the sensing element minimizes the induced stress concentration. Accordingly, in some embodiments, the respiration sensor 106 employs strain sensors using organic semiconductors, in particular using pentacene, and more particularly using a pentacene-carbon nanotube (CNT) composite. FIG. 2A shows that the output signal of a strain sensor in which CNTs are combined with pentacene is amplified considerably with the addition of CNTs, thus indicating the improvement in conductivity of the active layer. Addition of CNTs is particularly effective when the CNTs are added in the presence of toluene instead of water, which may be due to improved chemical bonding between the CNTs and pentacene in the presence of toluene. Further information regarding strain sensors built using flexible organic semiconductors can be found in Jung et al. (Jung, S., Ji, T., & Varadan, V. K. (2006), Smart Mater. Struct. 15:1872-1876), which is incorporated herein by reference in its entirety. In various embodiments, the respiration sensors 106 or other sensors or electrodes may be integrated into the fabric, e.g. by being woven into or printed on the fabric. Printing may be accomplished, for example, using an inkjet-type process.

Figure 2B:
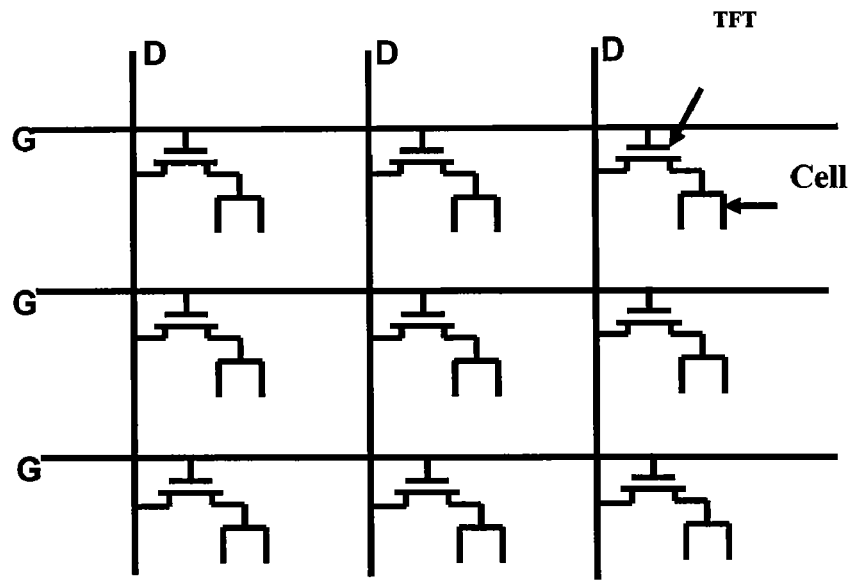
FIG. 2B shows an array of individually-addressable strain sensors using a thin-film transistor active matrix array.
Figure 2C:
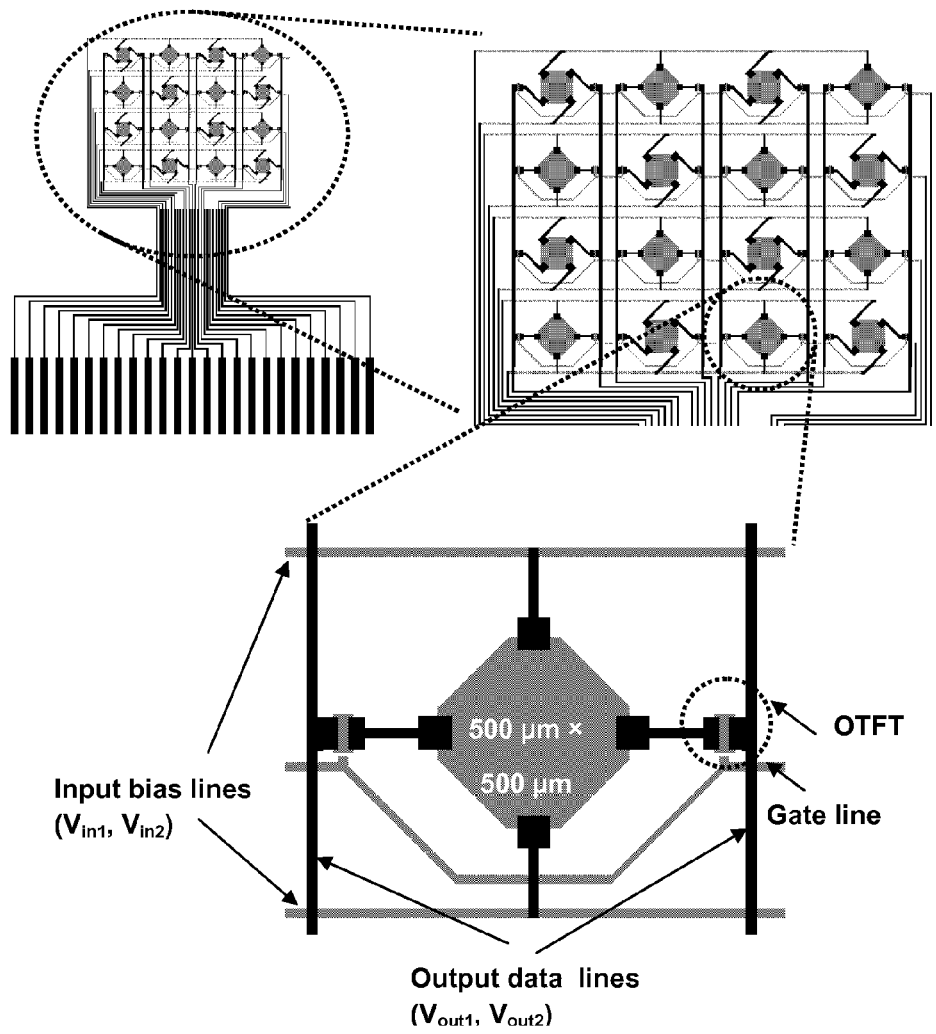
FIG. 2C shows an array of individually-addressable strain sensors using a thin-film transistor active matrix array at several levels of detail.

In various embodiments, the CNT-based strain sensors are implemented as arrays of sensors, each of which can be individually addressed for measurements using a thin-film transistor (TFT) active matrix array as shown in FIG. 2B. A row of pixels is selected by first applying appropriate voltages to the TFT gate (G) connected to the row of interest. Desired voltages are then applied to each pixel through the data lines (D) to read the data from each sensor cell. Non-selected pixels are isolated from the voltage operation of the selected pixels. Therefore, the TFT active matrix can be considered as a switch for selecting and isolating the pixels (i.e. sensors) for purposes of performing measurements from the individual sensors. FIG. 2C shows a schematic view of a 4×4 sensor array consisting of an organic TFT (OTFT), sensing elements, and input and output data lines based on the active matrix configuration. Measurements are obtained from the carbon nanotube-based strain sensors of the respiration unit by calibrating the change in electrical resistance due to the expansion and contraction of the chest. The differential resistance is measured and the signal from the sensors is amplified. This signal is fed to the wireless system after which it is digitized and stored.

Thus, the PMU 10, according to one embodiment, provides unobtrusive measurement of numerous biological parameters through the use of electroencephalography (EEG), electrocardiography (ECG/EKG), electrooculography (EOG), surface electromyography (sEMG), as well as measurements of respiration, temperature, and motion of a patient, including while the patient is asleep.

Figure 2D:
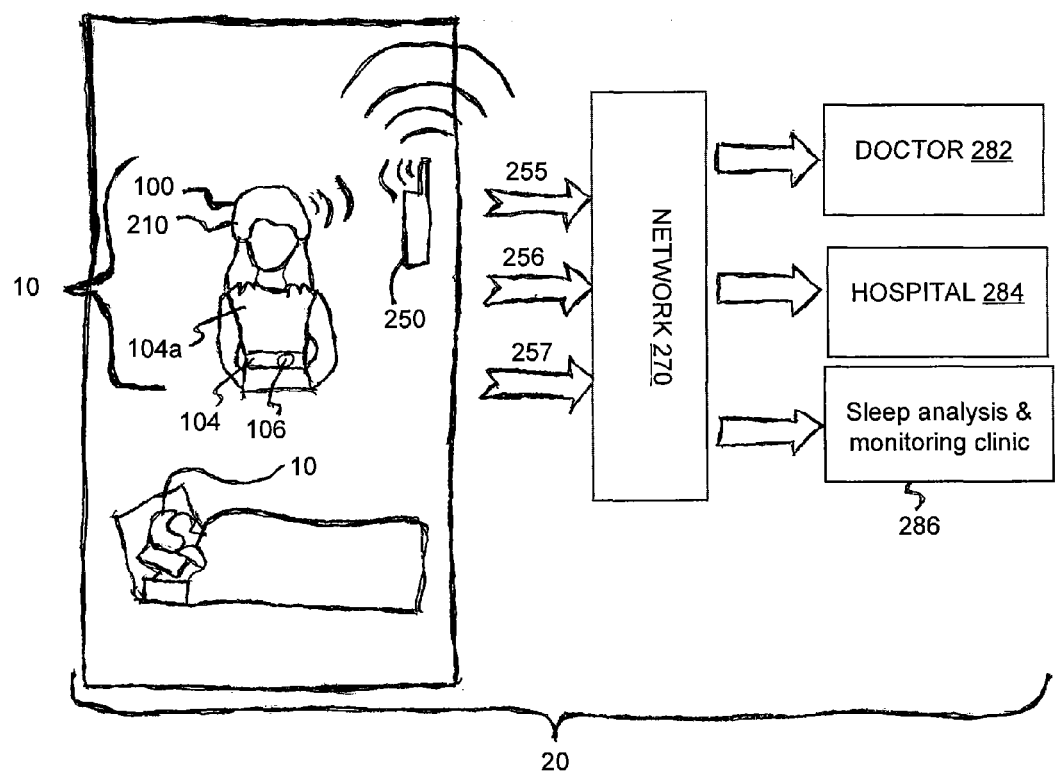
FIG. 2D shows an overview of a wireless system for patient monitoring.

In various embodiments of the invention, the PMU 10 may be implemented as part of a comprehensive remote patient monitoring system 20 as shown in FIG. 2D. FIG. 2D depicts the relationships between the various elements of the remote patient monitoring system 20, which includes the above-described PMU 10 in communication with a base receiver and server unit (BRU) 250, for example using a wireless communication standard such as Bluetooth® or a wireless mesh network standard such as ZigBee®. An advantage of Zig-Bee® is that this standard can support a network having over 65,000 nodes, thus the PMU 10 can include many elements (sensors, electrodes, etc.) and multiple patients, each with her own PMU 10, can be supported at a single monitoring location using the same Zigbee® network. Nevertheless, the use of other wired or wireless communication methods, including radio- or optical-based wireless communications, is also contemplated. Where the system employs a mesh network such as ZigBee®, each sensor of the PMU 10 may communicate independently with the BRU 250, and thus each sensor may be a separate unit that can be added to the PMU 10 independent of the other sensors, creating a modular system that can readily be customized for each patient and each application. Alternatively, the headcap 100 may utilize a single wireless module and antenna 108, as shown in FIG. 1A, so that all of the sensors in the headcap 100 communicate using the same wireless module and antenna 108. Similarly, the belt 104 may include a single wireless module and antenna to communicate information from the belt 104 to the BRU 250. Each component may have its own power supply or a central power source may supply power to one or more of the components of the PMU 10.

Figure 5:
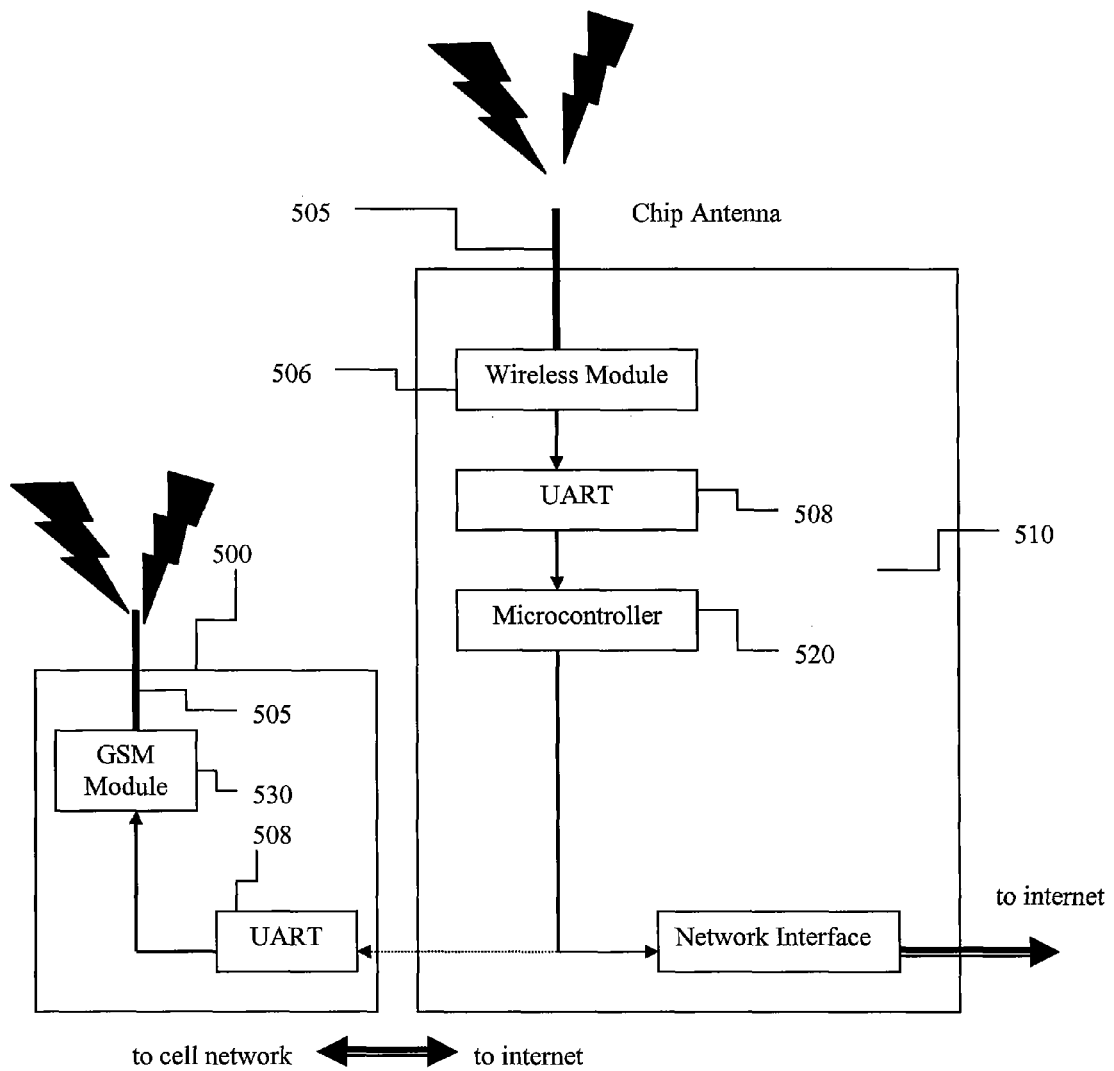
FIG. 5 shows a block diagram of the components inside the base receiver and server unit.

The BRU 250 acts as a hub, communicating via a network 270 such as the Internet to one or more of a doctor 282, a hospital 284, a sleep analysis and monitoring clinic 286, or other remote, centralized location or entity. In one embodiment, the BRU 250 is connected to the network 270 using a TCP/IP protocol 255 as shown in FIG. 5. The BRU 250 can also connect to a cellular telephone network 256 using a wireless network based on, e.g. the GSM/GPRS standard. Alternatively, the BRU 250 may communicate using one or more other wired or wireless mechanisms 257. In various embodiments, the PMU 10 may communicate directly with the network 270, for example using a GSM/GPRS-based cellular mechanism built into the PMU 10. In various embodiments, the remote location or entity (e.g. 282, 284, 286) includes a client monitoring application (CMA) for collecting, storing, analyzing, and displaying data (discussed further below).

The system unobtrusively measures biopotentials using patches of material containing a plurality of nanowire or nanotube integrated electrodes 102, which are referred to as "dry" sensors or "dry" biopotential electrodes. This eliminates the need for the application of conducting gels between a biosensor electrode and the patient's skin in order to obtain surface electrical recordings which is required for conventional electrodes in use today. Nevertheless, the system also can utilize conventional "wet" or "gel-based" electrodes which use conductive gel to promote electrical contact between the patient's skin and the electrode.

The dry sensor electrodes may be based on either carbon nanotubes or gold nanowires integrated with the amplifier in the headcap 100. In various embodiments, the nanotubes or nanowires are grown on a conducting substrate such as titanium (Ti), typically at a density of about $10^3$ per square centimeter, although higher or lower densities are also possible. In one embodiment, the nanotubes/nanowires are approximately 100 nm in diameter (range is 20-200 nm diameter in various embodiments) and are present at densities of $10^3$-$10^5$ per square centimeter. FIG. 1E shows a diagram of a plurality of aligned nanowires attached to a metal thin film which in turn is on a substrate such as silicon. The substrate/metal thin film/nanowire combination in some embodiments forms an electrode that is placed adjacent to the patient's skin to sense and record electrical signals, as discussed herein. The tips of the nanowires (or nanotubes) make contact with the patient's skin. In general, a patch of material may range in area from 1 mm$^2$ to 10 cm$^2$, although other sizes are also possible. Typically the patches of material are placed on a region of bare skin in order to maximize contact between the tips of the nanostructures and the skin.

The sensors and electrodes are interfaced to an analog-to-digital (A/D) converter in the PMU 10 using a drive circuit. The interface of op-amps and other types of amplifiers to A/D converters involved careful consideration of several characteristics of the amplifier and the requirements it placed on the data acquisition system. In addition to amplification, the EEG module also performed signal conditioning and filtering functions. The A/D converter was chosen and configured in accordance with the output signal characteristics of the amplifier module.

An ultra-low noise amplifier with high input impedance is generally used for EEG recordings, which are typically measured in microvolts (μV). To satisfy this requirement, the input stage of the amplifier is generally designed using metal-oxide-semiconductor field-effect transistors (MOSFETs). However, using a MOSFET to amplify a very low input signal, the noise has to be controlled, particularly the flicker, or "1/f," noise. The low impedance nature of the nanowire and carbon nanotube electrodes in the present invention helps to reduce the input impedances and hence obtain a better signal-to-noise ratio. Impedances between the dry nanowire- or nanotube-based electrodes and the amplifier inputs (which for an EKG measurement can be 5 kohm) can be matched by adjusting the density of nanostructures and/or the surface area of the patches containing the nanostructure sensors. With conventional gel-based electrodes, the conductive gel helps match the impedance by reducing resistance between the patient's skin and the electrode.

Figure 3:
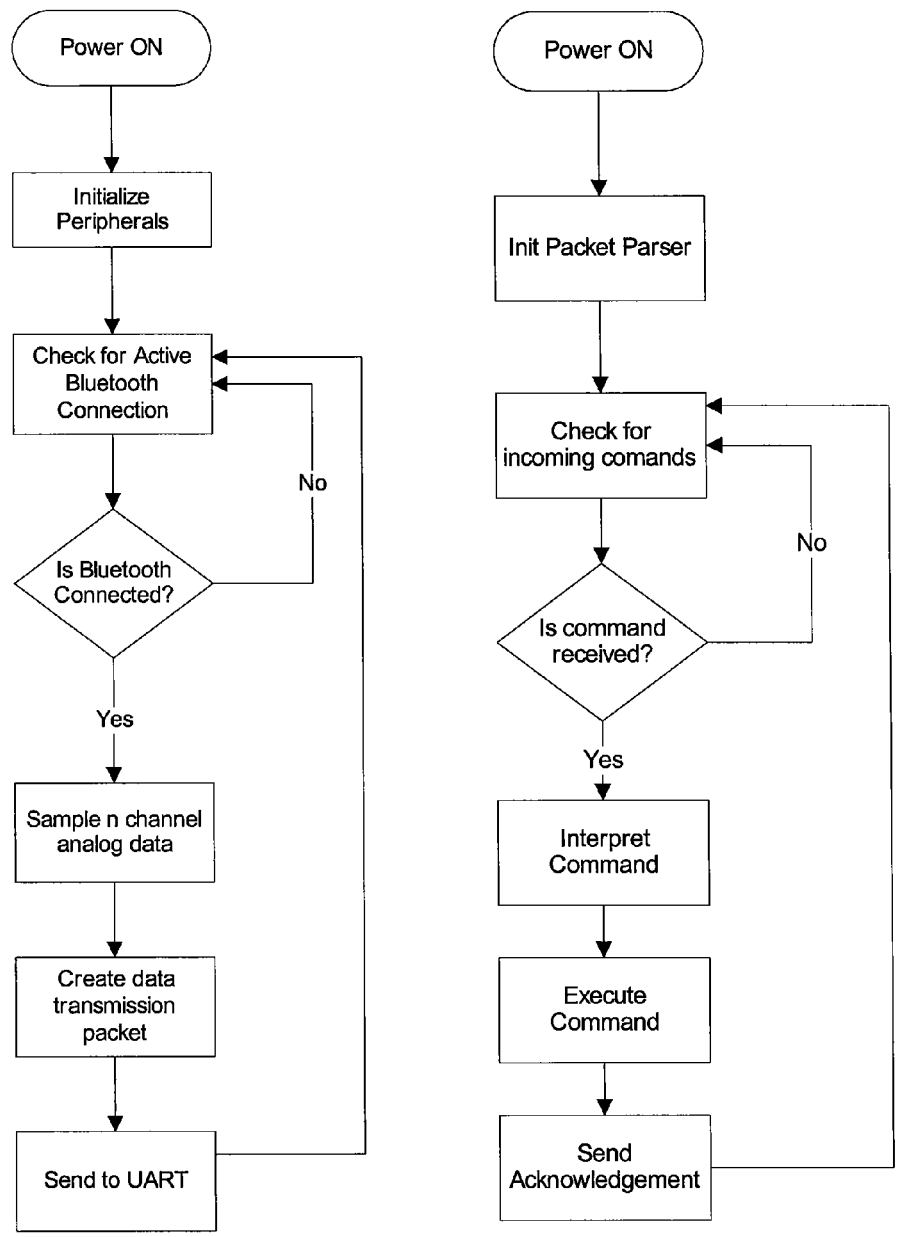
FIG. 3 shows a flow chart outlining software operations of the patient monitoring unit.
Figure 4:
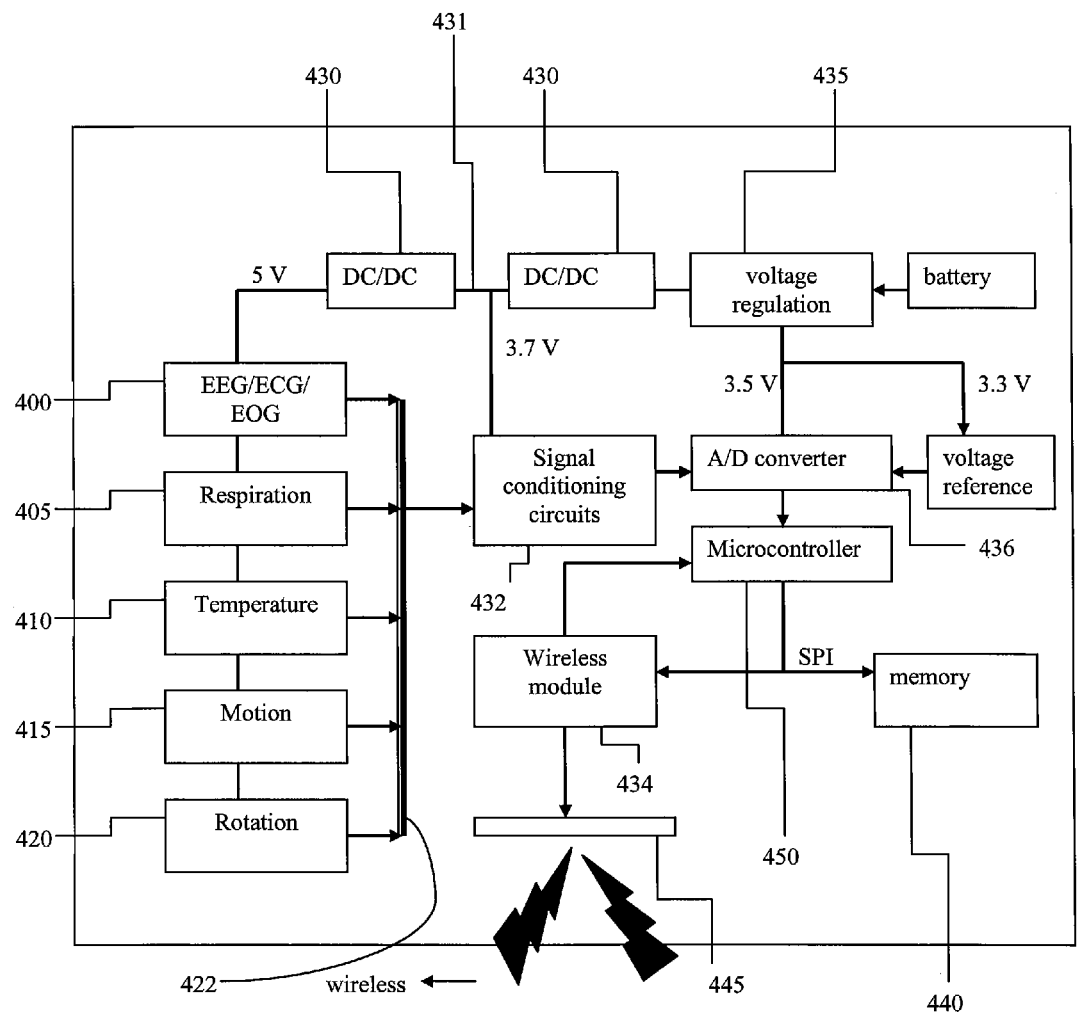
FIG. 4 shows a block diagram of the headcap with one possible configuration of sensors.

FIG. 3 presents a flow chart of operations for an embodiment of the PMU 10 which includes Bluetooth® communications. Software for the PMU 10 is based on a real-time operating system (RTOS) executing two parallel tasks. The send task (FIG. 3, left) is responsible for sampling analog input channels, formatting and creating a proper data packet format and for sending it to the universal asynchronous receiver/transmitter (UART) for transmission to the Bluetooth® module. After powering on and initializing peripherals, the send task checks for an active Bluetooth® connection. If a connection is detected, then n channels of analog data are sampled, a data transmission packet is created, and the packet is sent to the UART. The receive task (FIG. 3, right) is capable of responding to commands from the central monitoring system. After powering on and initializing peripherals, the receive task checks for incoming commands. If a command is received, then the command is interpreted and executed, and an acknowledgement is sent. A command interpreter is implemented to allow for interpretation and execution of commands such as those to start/stop transmission and for setting system parameters such as sampling frequency, channels, and other system-specific functions. The real-time operating system codes are used to control the data input and output along with data management, which is written inside the microcontroller 450 (FIG. 4). The real-time operating system was developed in such a way that the time required to handle these operations can be reduced.

Figure 8:
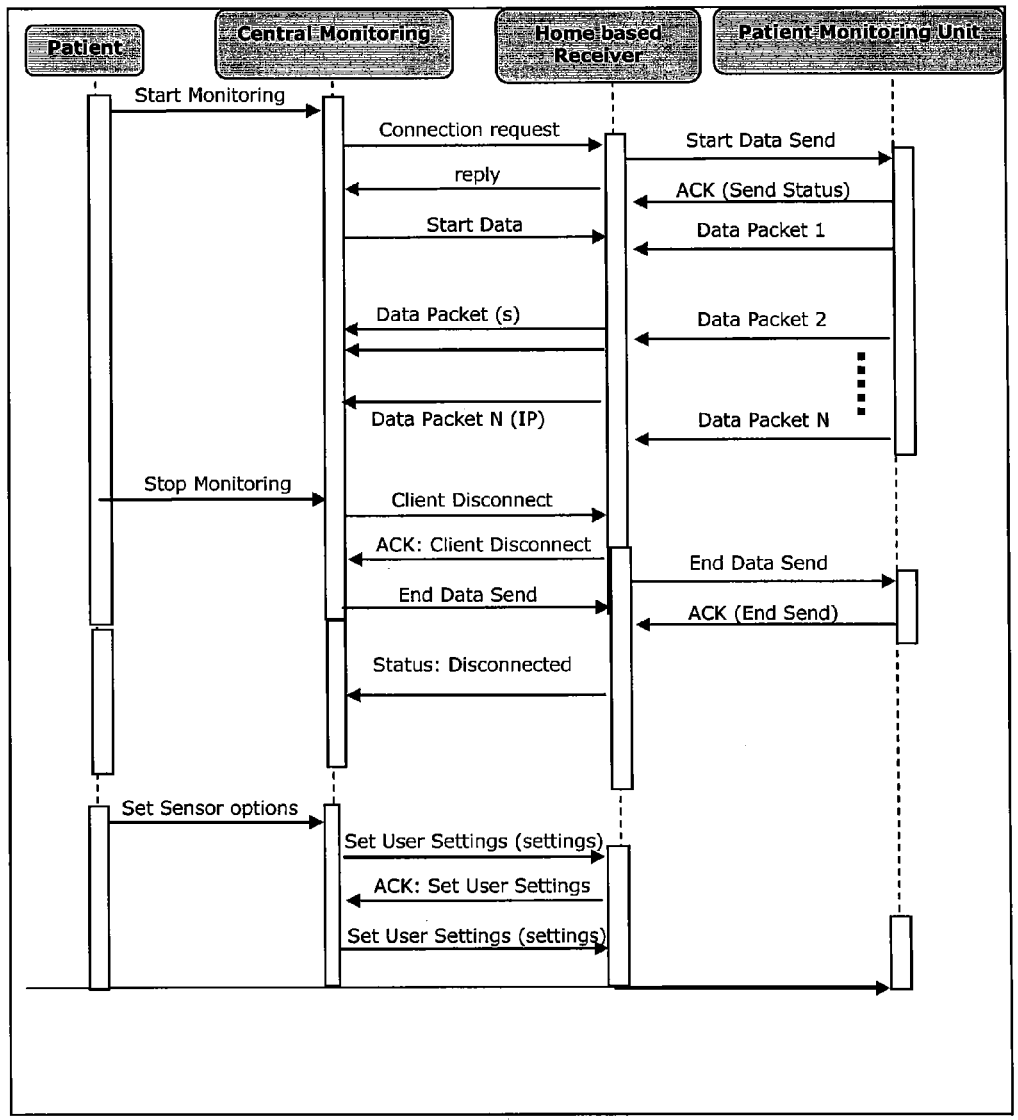
FIG. 8 shows data flow sequences programmed in the microcontroller.

Referring to FIG. 4, in the schematic circuit of the headcap 100, the analog signals from the sensors such as biopotential electrodes 400, respiration sensor 405, temperature sensor 410, motion sensor 415, and rotation sensor 420 are fed 422 into signal conditioning circuits 432. The output from the voltage regulator 435 is given to various DC/DC converters 430 at different stages for the generation of required DC voltages as well as for reference voltages. These signals are digitized using A/D converters 436. A microcontroller 450 mainly controls the data flow as shown in FIG. 8 by using the embedded real-time operating system codes. The microcontroller 450 also controls the wireless range and the data flow. In various embodiments, a warning or alarm signal is generated if the headcap 100 is out of range from the BRU 250.

As clear from the schematic FIG. 4, the microcontroller 450 gives preference to wirelessly transmit the real-time data after establishing a necessary wireless connection. However, if the connection is failed or broken while transmitting the data to the BRU 250, the data will be saved in the memory module 440 using a system packet interface (SPI). The wireless module 434 is a ZigBee® mesh networking device, which is integrated to the chip antenna 445. The details of the signal conditioning circuits 432 are explained in respective sections. Accurate EEG measurement and its digitization is implemented in this system using the necessary reference voltages and the isolation of the power plane from the signal plane. This system is implemented in a four-layer printed chip. Element 422 is the signal bus line and 431 is the power bus line.

FIG. 5 shows an embodiment of BRU 510 which is built around an ARM Single Board Computer. In this application, the ZigBee® wireless communication module 506, along with microcontroller 520 and antenna 505, is connected to BRU 510 through a regular UART COM port 508 (FIG. 5, right). The unit is also connected to another computer network such as the Internet through a built-in Ethernet interface (FIG. 5, right). The cellular network connection 500 achieved in BRU 510 uses UART 508 and a GSM communication module 530 and antenna 505 (FIG. 5, left).

Figure 6:
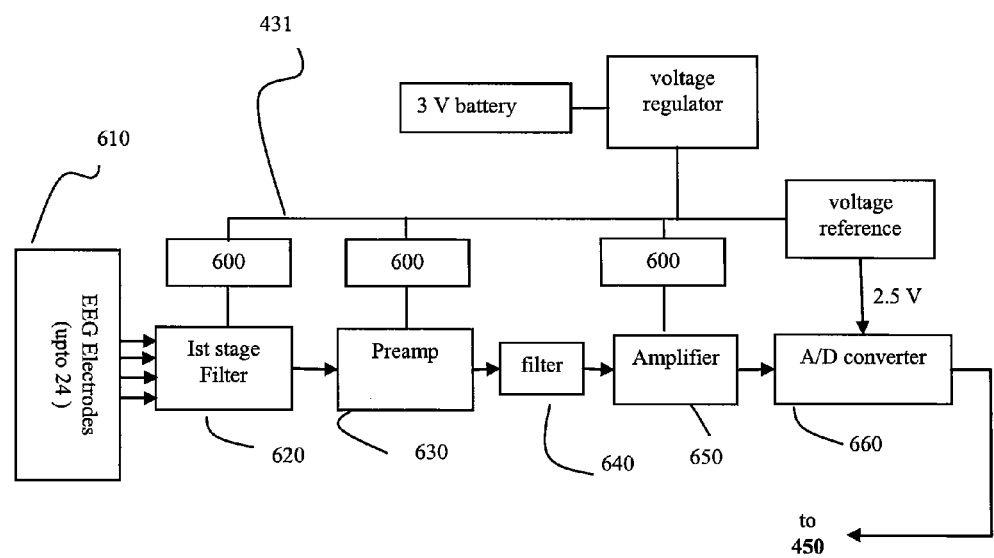
FIG. 6 shows a block diagram of the electronic circuit developed to measure EEG, ECG/EKG and EOG using nanowire integrated electrodes along with the precision voltage distribution network.

An embodiment for the EEG/EKG/EOG measurement using conventional based wet-gel and/or dry nanowire and nanotube integrated biopotential electrodes is presented in FIG. 6. The electrodes 610 are connected to a first stage filter circuit 620 before preamplification and filtering. The preamplifer 630 amplifies the signal twelve-fold and then filters unwanted frequency bands using active filter 640. The final amplifier 650 has two stages so that it amplifies the signal another six hundred-fold. Other levels of amplification are possible and depend on the factors such as the electrodes that are used. This amplified signal is then fed to A/D converter 660 and then to microcontroller 450. This circuit is powered using a 3V battery and necessary voltages are regulated and controlled by DC/DC converters 600.

Figure 7:
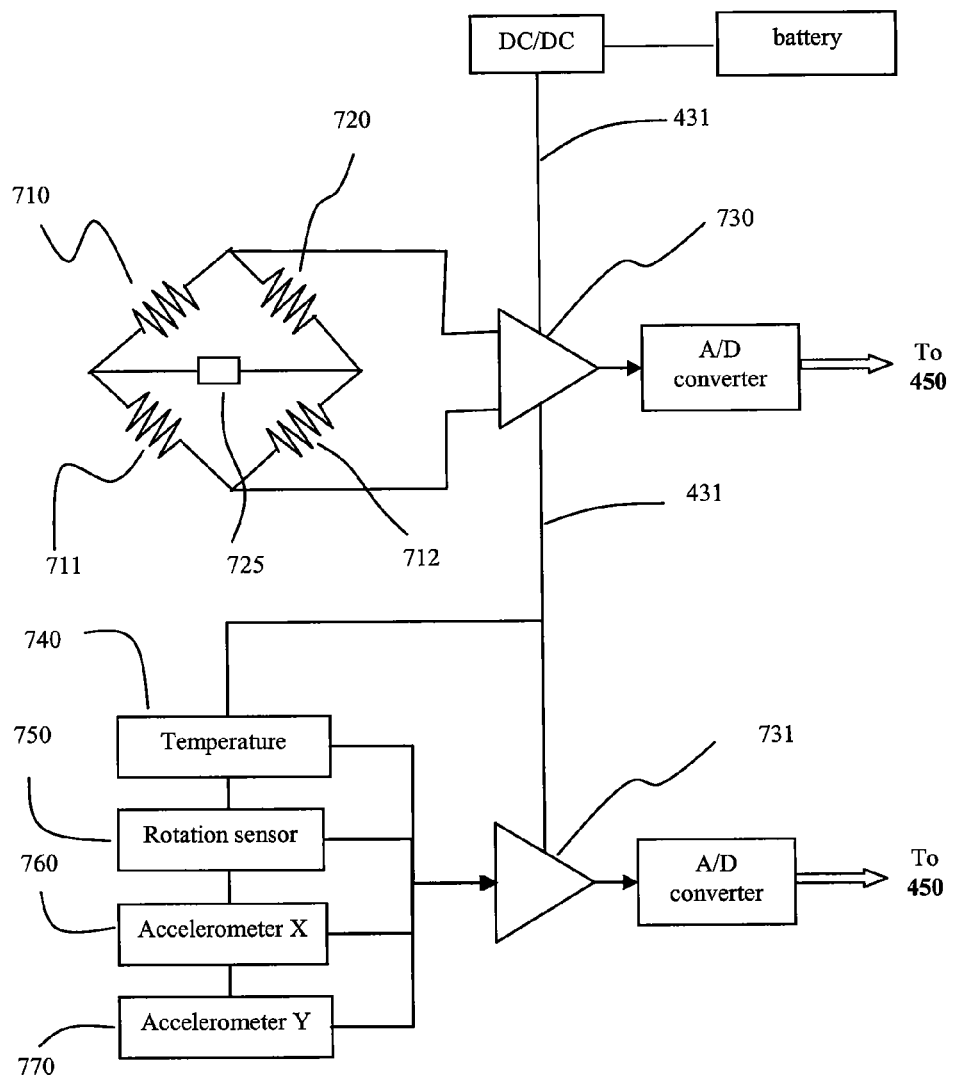
FIG. 7 shows a schematic diagram of the carbon nanotube respiration sensor circuit and a circuit diagram for the temperature and motion sensors.

FIG. 7 schematically represents the respiration sensor circuits, temperature, and motion sensors circuits integrated into the headcap. It is useful to monitor a patient's body and/or head movements while the patient is asleep to monitor any abnormalities in movement parameters. The movement in this case was monitored by two accelerometers 760 and 770 to measure X and Y movement, respectively, and by a gyroscope 750 to measure rotational motion. The temperature sensor 740 continuously monitors the body temperature of the patient. The data from these three sensors are used to correlate and to compute the patient's body movements so that the body movements can be classified.

Body temperature is an important parameter for assessing the condition of a sleeping patient. Sudden changes in body conditions are usually accompanied by a change in body temperature and hence the temperature can be used a factor, in combination with other parameters, for assessing the patient's physical state. This is particularly important for the monitoring of elderly patients. The temperature sensor 740, which can be any of a number of commercially-available designs, outputs a voltage proportional to the temperature applied to it, which can be calibrated to a temperature in Celsius or Fahrenheit. The operating temperature range was adjusted according to the particular application by the use of external resistors. In some embodiments, the temperature sensor is a thin film transistor-based temperature sensor as disclosed by Jung et al. (S. Jung, T. Ji, and V. K. Varadan, "Temperature sensor using thermal properties in the subthreshold regime of an organic thin film transistor", Applied Physics Letters, 90, pp. 062105-062110, 2007, incorporated herein by reference in its entirety).

In certain embodiments, the respiration sensor 720 is a carbon nanotube-based respiration sensor which changes the resistance due to expansion/contraction of the patient's chest, as discussed above. The differential amplifier 730 amplifies the minute changes in the resistance from the balanced circuit using regular resistors 710, 711, 712, and a constant power source 725. Amplifier 731 amplifies the signals from sensors 740, 750, 760, and 770. The output of amplifiers 730 and 731 are digitized by A/D converters and the outputs fed into microcontroller 450. Although the input and output of amplifier 731 are shown as single lines, in practice separate lines are used to transmit signals from sensors 740, 750, 760, and 770 to the A/D converter and to the microcontroller 450.

A circuit such as is shown in FIG. 4 is constructed to supply accurate voltages to the sensor systems using DC/DC converters 430. The power bus line 431 powers the sensors and the A/D converters.

In certain embodiments, the system also includes a mechanism for the detection and indication of any interruption in real-time monitoring due to communication problems (such as the PMU 10 being out of range of the BRU 250), for example if the wireless signal strength drops below a predetermined threshold level. A display on the BRU 250 could inform the patient when they are being monitored. The patient needs to be alerted to any interruptions in communications. In addition, the system can also provide a real-time health estimate returned by the central monitoring system, which is calculated based upon the parameters being monitored.

FIG. 8 presents a detailed sequence diagram of the request-response protocol used in embodiments of the invention. To start monitoring, the patient initially registers with a doctor, hospital, sleep clinic, or other entity in order to participate in home-based sleep or other health monitoring. The patient registers through a secure means, such as direct face-to-face contact, a secure Internet or other network connection. The patient is given a unique code which is used to identify the patient and their data within the system. The patient's identifying code, which can be a series of stored numbers and/or letters, may be encoded in a barcode or RFID chip, in which case the code may be transmitted with an appropriate barcode or RFID reader. The central monitoring server is initially in a listening mode, where it creates a TCP/IP server socket and waits for a patient/client to connect. As shown here, the connection is initiated when the client or the central monitoring program sends a request to the BRU to start the monitoring process. The home based receiver unit then creates a connection with the patient monitoring unit which then starts sending the sensor data back. This data is then relayed onto the client program by the BRU. After disconnection, the server goes back into the original listening mode. Functions are also available to set sensor options such a number of channels, sampling rate, channel order etc. through the client monitoring program itself. This control information is then relayed to the patient monitoring unit through the home based receiver unit.

Figure 9:
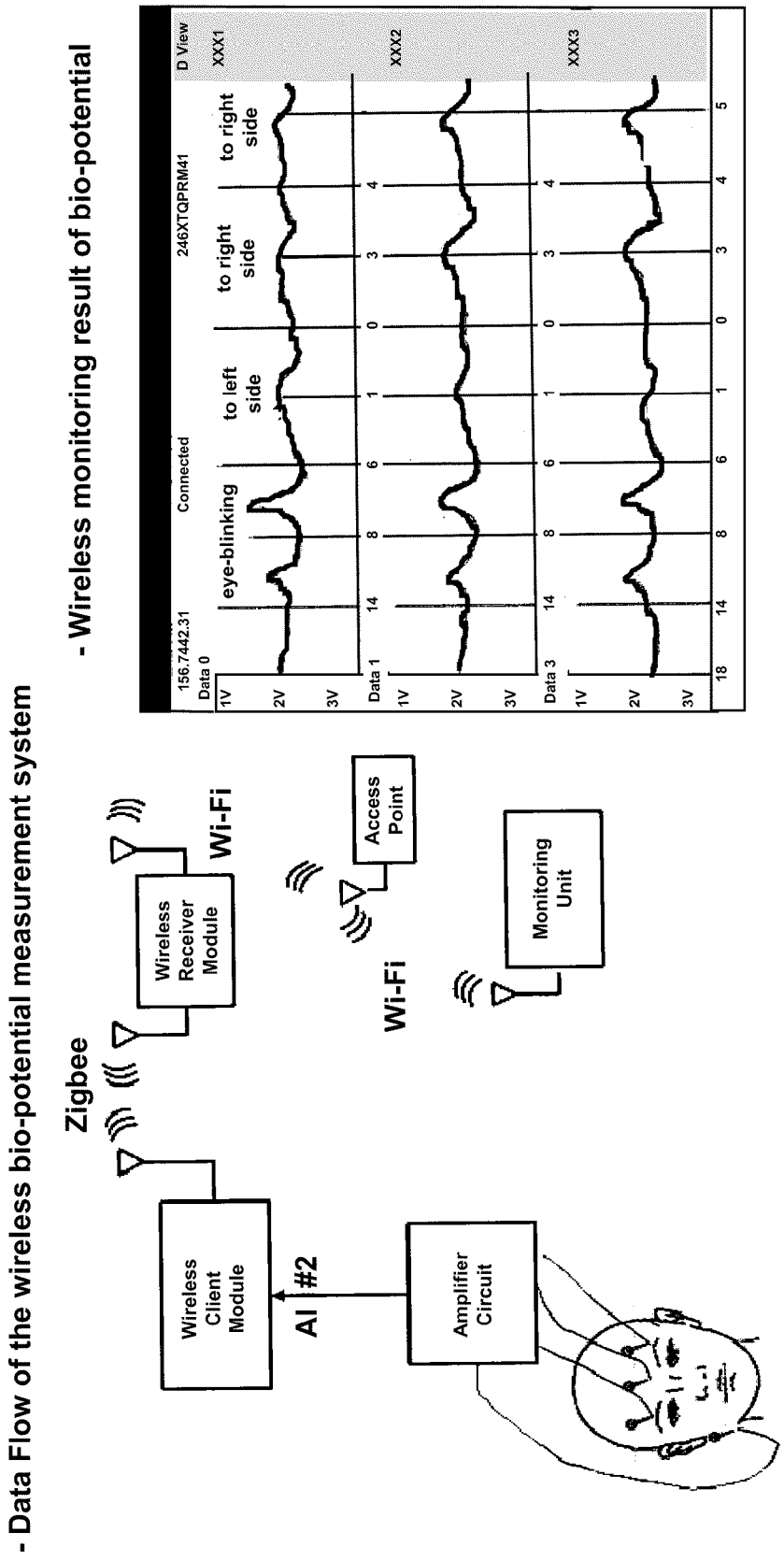
FIG. 9 shows data flow in the system and the measured data at a remote location.

The right-hand portion of FIG. 9 presents an example screen shot of the measured data obtained at a remote patient monitoring location using a system, e.g., as shown in the left-hand portion of FIG. 9. The screen shot, for example, might be part of a client monitoring application and would viewed at a hospital, doctor's office, sleep research clinic, or other central monitoring facility. The data in the right-hand portion of FIG. 9 is presented for EEG, ECG, motion, respiration, rotation and temperature measured for a volunteer.

Figure 10:
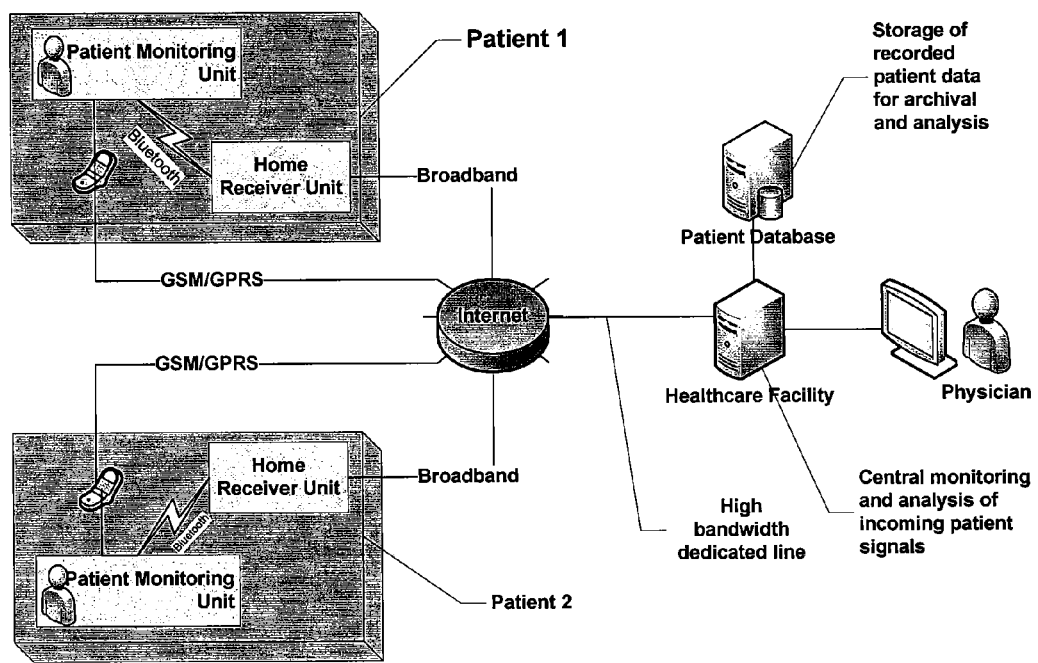
FIG. 10 shows an overview of a patient monitoring and assessment system.

FIG. 10 shows an overview of a patient monitoring an assessment system according to an embodiment of the invention in which two patients are remotely monitored. For each patient, the PMU 10 can communicate with the network (Internet) either through the home receiver unit to a broadband connection or directly to the network via a cellular network, e.g. using a GSM/GPRS connection. Data is transferred over the network to a computer at a healthcare facility where it can be viewed and analyzed by a physician and/or archived in a patient database for later retrieval and analysis.

EXAMPLE

Described below is a non-limiting example of the elements of a patient monitoring and assessment system according to an embodiment of the invention.

Power Supply Design

Power supply was one of the most important aspects of the circuit, so careful consideration was given to the design and layout of power supply components. The power source is an important consideration in the design of any kind of wearable device, but it is also important to keep the battery small enough to reduce size and weight of the device. Lithium Ion/Lithium Polymer batteries provided a good source of power with a high milliamp-hour (mAh) rating while being relatively light and small in size. These battery packs provided a standard output voltage of 3.7 V with 1000-2000 mAh capacity, with dimensions approximately 40 mm×20 mm×5 mm. These specifications made it suitable for use in wearable and portable devices. Since most of the components used in the design required a 5V power supply, a step-up DC-DC converter circuit was used to step-up the 3.7V voltage provided by the battery.

The microcontroller circuit with the ZigBee® module and their supporting components were powered from a 3.3V supply rail.

Digital portions of the ADCs were powered by a 5V supply rail.

Analog portions of the ADCs and the attached EEG module were powered another 5V supply rail.

Software Design

In the implementation of a sleep monitoring unit, a different approach was used to implement real-time functionality. A real-time operating system (RTOS) was used to achieve near deterministic response to events and precisely timed execution of software routines. The RTOS allowed different functions of a program to be implemented as different tasks. Priorities were assigned to each task and the RTOS scheduler was responsible for task switching and deciding which task was to be given priority of execution. While an RTOS can provide several other services such as communication stacks and memory management besides scheduling, only the scheduler (or real-time kernel) was required.

In this embodiment, the RTOS is implemented in the system with concurrent processes, each performing different functions. The processes implemented here were the SendData thread and the ReceiveData thread, which are described further below.

The SendData thread handled the transmission of data and command packets to the remote device. Its main functions included serialization of data into packets for reliable transmission, application of appropriate packet format to raw data depending upon whether it is a data or command packet, computation of checksum for error detection at the receiver end, and actual bitwise transfer of the data to the wireless module in the required format. The data to be transmitted was buffered in a queue data structure and transmitted to the wireless module in a first-in-first-out (FIFO) manner. The SendData thread had the highest thread priority among the running threads, as error-free transmission of data was the most important function.

The ReceiveData thread listened for incoming command packets from the central monitoring system. It received and interpreted commands such as those to start/stop transmission, change sampling rate or data rate, change number of channels to be sampled among several others. It had a state machine based model to receive the packet data in units of transmission and then reassemble them into a command which was then passed on to the command interpreter module also implemented in the same thread.

Base receive-transmit unit (BRU)/Home-Based Receiver Unit

In some embodiments the BRU 250 is part of a comprehensive home-based receiver unit, which may also include components such as memory, a hard drive, and/or a controller. The home-based receiver unit may collect all of the raw data from the PMU 10 but transmit only a reduced amount of information to the CMA. For example, the home-based receiver unit may transmit a time-based average of a parameter, the high and or low value of a parameter for a time period, or only transmit a value when a parameter is outside of a predetermined limit. At some point, all of the data from the home-based receiver unit can be recovered, for example remotely (e.g. over the Internet or other connection) or by direct transfer (e.g. direct connection of unit to a server or by manual transfer of memory media such as a hard drive or memory stick). The home-based receiver performs the functions of receiving sensor data from the PMU and relaying the data through a data network to the client application. It was designed to be a compact, head-less (i.e. no user interface) unit which was easy to configure and use. To reduce size and cost, the system was built around a single board computer with all required capabilities built into it. The BRU acts a server in a client-server situation and provided connections to clients (which, in this case was the central monitoring system) which streamed data from this unit.

Communication

A custom request and response protocol was developed for data and control communication between the two units. The server is initially in a listening mode, where it creates a TCP/IP server socket and waits for a client to connect. The connection is initiated when the client or the central monitoring program sends a request to the server (home based receiver unit) to start the monitoring process. The home based receiver unit then creates a connection with the patient monitoring unit which then starts sending the sensor data back. This data is then relayed onto the client program by the home receiver unit. After disconnection, the server goes back into the original listening mode. Functions are also available to set sensor options such a number of channels, sampling rate, channel order etc. through the client monitoring program itself. This control information is then relayed to the patient monitoring unit through the home based receiver unit.

The ZigBee® module was connected to the single board computer (SBC) through one of the available onboard serial ports. The SBC provided access to this port through the header marked COM2. Power for the Bluetooth® module was also obtained through the 5V supply and ground lines available in the header marked LCD.

Client Monitoring Application (CMA)

The CMA is a Windows-based application running on a networked PC with access to the central monitoring server. It acts as a TCP/IP client application which connects to a TCP/IP socket of the remote server on the network port which is specified. In general, a client monitoring unit includes a computer system with a storage medium (e.g. hard disk, memory, and the like) on which the CMA is stored. The client monitoring unit includes a processor which is operably coupled to a network (e.g. the Internet). The CMA includes program instructions which are executable by the processor for receiving and processing data from the PMU, among other functions, and can be installed on the storage medium. Among various features, the CMA is programmed to:

(1) Connect to a remote server socket specified by the user.

(2) Receive the data in the packet format of the patient monitoring unit and extract data from the packet, while checking reliability of the data using the checksum value transmitted as part of the packet by the remote unit.

(3) Visualize the data using multiple real-time plots for all of the channels.

(4) Log in the received data to a file for further processing.

(5) Apply a user-assignable digital filter for the input data.

The central monitoring system software was developed using Microsoft Visual Studio.net base on the Microsoft.net framework. Custom Windows forms controls were developed and used for real-time visualization of the incoming data. An input data buffer buffered the incoming data before it was ready to display to ensure that none of the data was lost when the program responded slowly during the drawing.

Although the present invention has been described in detail with reference to the preferred embodiments, it will be understood by those of ordinary skill in the art that various modifications can be made without departing from the scope of the invention.

What is claimed is:

1. A wireless system for neurological and physiological monitoring of a patient, comprising:
a patient monitoring unit comprising a headcap and a belt,
the headcap including a wireless communication module, an antenna, and an amplifier, further including
a biopotential electrode,
a temperature sensor,
a rotation sensor,
an accelerometer, and
an airflow sensor,
the belt including
a respiration sensor comprising a flexible and printable nanotechnology-based strain sensor,
a base receiver-server unit including
a wireless receiving unit,
a data storage unit, and
a network communications unit, and
a client monitoring unit including
a processor,
a network communications unit operably coupled to the processor, and
a storage medium operably coupled to the processor, wherein the storage medium includes program instructions executable by the processor for receiving and processing data from the patient monitoring unit.

2. The wireless system of claim 1, wherein the biopotential electrode is configured to measure at least one of an electroencephalogram (EEG) and an electrooculogram (EOG).

3. The wireless system of claim 1, wherein the temperature sensor comprises a thin film transistor-based temperature sensor.

4. The wireless system of claim 1, the system further comprising a leg monitoring unit, the leg monitoring unit including at least one accelerometer to measure leg motion.

5. The wireless system of claim 1, wherein the flexible and printable nanotechnology-based strain sensor of the belt of the patient monitoring unit comprises a pentacene-carbon nanotube composite organic semiconductor.

6. The wireless system of claim 1, wherein the belt further comprises a plurality of biopotential electrodes configured to monitor an electrocardiogram (ECG/EKG).

7. The wireless system of claim 6, wherein the biopotential electrode comprises at least one of a flexible and printable nanotechnology-based sensor, a dry carbon nanotube array-based electrode, and a dry gold nanowire array-based electrode.

8. The wireless system of claim 1, wherein the biopotential electrode comprises at least one of a flexible and printable nanotechnology-based sensor, a dry carbon nanotube array-based electrode, and a dry gold nanowire array-based electrode.

9. The wireless system of claim 1, wherein one or more biopotential electrodes are separate from either the headcap or the belt.

10. The wireless system of claim 1, wherein the wireless communication module, antenna, and amplifier are housed in a form factor that is embedded in at least one of the headcap and the belt.

11. The wireless system of claim 1, wherein the wireless communication module, antenna, and amplifier are housed in a form factor that is tethered to at least one of the headcap and the belt.

12. A patient monitoring unit for neurological and physiological monitoring of a patient, comprising: a headcap including a wireless communication module, an antenna, an amplifier, a biopotential electrode, a temperature sensor, a rotation sensor, an accelerometer, and an airflow sensor, the patient monitoring unit further comprising a respiration sensor including a flexible and printable nanotechnology-based strain sensor.

13. The patient monitoring unit of claim 12, wherein the biopotential electrode is configured to measure at least one of an electroencephalogram (EEG) and an electrooculogram (EOG).

14. The patient monitoring unit of claim 12, wherein the temperature sensor comprises a thin film transistor-based temperature sensor.

15. The patient monitoring unit of claim 12, the system further comprising a leg monitoring unit, the leg monitoring unit including at least one accelerometer to measure leg motion.

16. The patient monitoring system of claim 12, wherein the flexible and printable nanotechnology-based strain sensor of the belt comprises a carbon nanotube-based strain sensor.

17. The patient monitoring unit of claim 16, wherein the belt further comprises a plurality of biopotential electrodes configured to monitor an electrocardiogram (ECG/EKG).

18. The patient monitoring unit of claim 17, wherein one or more biopotential electrodes are separate from either the headcap or the belt.

19. The patient monitoring unit of claim 17, wherein the biopotential electrode comprises at least one of a flexible and printable nanotechnology-based sensor, a dry carbon nanotube array-based electrode, and a dry gold nanowire array-based electrode.

20. The patient monitoring unit of claim 12, wherein the biopotential electrode comprises at least one of a flexible and printable nanotechnology-based sensor, a dry carbon nanotube array-based electrode, and a dry gold nanowire array-based electrode.

21. The wireless system of claim 1, wherein the flexible and printable nanotechnology-based strain sensor comprises at least one of a carbon nanotube-based strain sensor and a textile-based strain sensor.

22. The patient monitoring unit of claim 12, wherein the flexible and printable nanotechnology-based strain sensor comprises at least one of a carbon nanotube-based strain sensor and a textile-based strain sensor.

* * * * *